US006441133B1

(12) United States Patent
Walker

(10) Patent No.: US 6,441,133 B1
(45) Date of Patent: Aug. 27, 2002

(54) THYROTROPIN-RELEASING HORMONE RECEPTOR 2(TRHR-2)

(75) Inventor: Philippe Walker, Montréal (CA)

(73) Assignee: AstraZeneca Canada Inc., Mississauga (CA)

( * ) Notice: Subject to any disclaimer, the term of this patent is extended or adjusted under 35 U.S.C. 154(b) by 0 days.

(21) Appl. No.: 09/029,027

(22) PCT Filed: Nov. 28, 1997

(86) PCT No.: PCT/SE97/01999

§ 371 (c)(1),
(2), (4) Date: Jan. 27, 1998

(87) PCT Pub. No.: WO98/24818

PCT Pub. Date: Jun. 11, 1998

(30) Foreign Application Priority Data

Dec. 2, 1996 (SE) .............................................. 9604439

(51) Int. Cl.⁷ ...................... C07K 14/705; C07K 14/72; C07K 14/47; C07K 14/435
(52) U.S. Cl. ...................................... 530/350; 435/69.1
(58) Field of Search .......................... 530/350; 435/69.1

(56) References Cited

FOREIGN PATENT DOCUMENTS

| WO | WO 92/10565 | 6/1992 |
| WO | WO 94/29447 | 12/1994 |

OTHER PUBLICATIONS

Alexandrova, et al., "Two Novel Thioamide Analogues of TRH with Selective Activity on CNS," *Gen. Physiol. Biophys.* 10:287–297 (1991).

Boschi, et al., "Antinociceptive Properties of Thyrotropin Releasing Hormone in Mice: Comparison with Morphine," *Br. J. Pharmac.* 79:85–92 (1983).

Burt, "TRH Receptors," *Ann. NY Acad. Sci.* 553: 188–190 (1989).

de la Peña, et al., "Two Isoforms of the Thyrotropin–Releasing Hormone Receptor Generated by Alternative Splicing Have Indistinguishable Functional Properties," *J. Biol. Chem.* 267:25703–25708 (1992).

Duthie, et al., "Cloning and Functional Characterisation of the Human TRH Receptor," *Mol. Cell. Endocrinol.* 95:R11–R15 (1993).

Faden, "TRH Analog YM–14673 Improves Outcome Following Traumatic Brain and Spinal Cord Injury in Rats: Dose–Response Studies," *Brain Res.* 486:228–235 (1989).

Kaji, et al., "The Regional Distribution of Thyrotropin–Releasing Hormone Receptor Messenger Ribonucleic Acid in the Brain," *Neurosci. Let.* 151:81–84 (1993).

Matre, et al., "Molecular Cloning of a Functional Human Thyrotropin–Releasing Hormone Receptor", *Biochem. Biophys. Res. Comm.* 195:179–185 (1993).

Straub, et al., "Expression Cloning of a cDNA Encoding the Mouse Pituitary Thyrotropein–Releasing Hormone Receptor," *Proc. Natl. Acad. Sci. USA* 87: 9514–9518 (1990).

Toledo–Aral, et al., "Dual Modulation of K⁺ Currents and Cytosolic Ca² By the Peptide TRH and Its Derivatives in Guinea–Pig Septal Neurones," *J. Physiol.* 472:327–340 (1993).

Wu, et al., "Identification of Neurons Expressing Thyrotropin Releasing–Hormone Receptor mRNA in Spinal Cord and Lower Brainstem of Rat," *Neurosi. Let.* 142:143–146 (1992).

*Primary Examiner*—Michael Pak
(74) *Attorney, Agent, or Firm*—Michael A. Sanzo; Pillsbury Winthrop LLP

(57) ABSTRACT

The present invention is directed to the novel receptor for TRH which has been designated as TRH receptor 2. The invention encompasses both the receptor protein as well as nucleic acids encoding the protein. In addition, the present invention is directed to methods and compositions which rely upon either TRHR-2 proteins or nucleic acids.

8 Claims, No Drawings

SEQUENCE LISTING

<160> NUMBER OF SEQ ID NOS: 5

<210> SEQ ID NO 1
<211> LENGTH: 1600
<212> TYPE: DNA

<213> ORGANISM: Rat

<400> SEQUENCE: 1

| | | | | | |
|---|---|---|---|---|---|
| ctttaaacca | cagcctctca | aatacgcatc | cctacactgg | ctcctttctt | ggtcttccta | 60 |
| tctgagccct | gatggcttct | ccagctgctc | ttccagagac | ctgggttcaa | ttcccagcac | 120 |
| ctatatgaca | acttacagat | tggtggctgt | aactccaatc | cggggatgc | aatgccatct | 180 |
| tctggcctcc | agaggcacta | catacacaca | tgatacacag | aatatacaca | cgtgtatatt | 240 |
| taggtaaagt | gcctgtgcac | ataaaaaaaa | ataaaaagga | aaaaaattaa | atcagaagga | 300 |
| acaggcaccg | gtcacttacc | aaggtcaagg | cctacagggc | accacagaaa | acaccagcaa | 360 |
| gatggatggc | cccagtaatg | tctcgctcat | tcacggtgac | accacgctgg | gcctgccaga | 420 |
| gtacaaggtg | gtctcagtct | tcctagtgct | cctggtgtgc | accctgggca | tcgtgggcaa | 480 |
| tgccatggtg | attctggtgg | tgctgacctc | acgtgacatg | cacacaccca | ccaactgcta | 540 |
| cctggtcagc | ctggccctcg | ctgacctcct | cgtgctgctg | gctgcgggtc | tgcccaatgt | 600 |
| ctctgacagc | ctagtggggc | actggatcta | tggacgtgct | ggctgcttgg | gcatcaccta | 660 |
| cttccagtac | ctgggcatca | atgtctcctc | cttctccatc | ctggccttca | ctgtggagag | 720 |
| gtatatagcc | atttgccacc | cactgagagc | acagaccgtg | tgcactgtgg | cccgggccaa | 780 |
| acggatcatg | gcaggcatct | gggggtcac | gtccctctat | tgcctactct | ggttcttcct | 840 |
| ggtggatctc | aatgtccgtg | acaaccagcg | ccttgaatgt | ggctacaaag | tgccccgagg | 900 |
| actctacctg | cccatctacc | tgctggactt | cgctgtcttt | ttcatcggac | ccttgctggt | 960 |
| gacccctcgtg | ctctatgggc | tcatcgggag | gatttatttt | cagagcccgt | tgtcccagga | 1020 |
| agcctggcag | aaggagaggc | agccccatgg | gcagagcgag | gctgcaccag | gcaactgctc | 1080 |
| cagggccaag | agctccagga | agcaggccac | caggatgctg | gccgtggttg | tgttgctttt | 1140 |
| tgccgtgctg | tggaccccctt | accgcacact | ggtactgctc | aactcctttg | tggcccagcc | 1200 |
| tttcctggac | ccctgggtcc | tgctgttctg | ccgcacctgt | gtctacacca | acagcgctgt | 1260 |
| caaccctgtc | gtctacagcc | tgatgtcaca | gaagttccgg | gcggccttcc | tgaaactgtg | 1320 |
| ctggtgcagg | gcagctgggc | cacagcggag | ggcagcacgc | gtcctcacca | gtaactacag | 1380 |
| tgccgcccag | gagacctcag | aaggaactga | gaagatgtag | ctgggctcca | gtgaggtctc | 1440 |
| aggtcccacg | gcagcaggtc | ccctggcctg | tcagcatgag | ccctacttca | gtgtgctctg | 1500 |
| aggactcccg | cctggcccct | gaccccgctt | aaggcttggt | tggcatttgg | gaggcatcag | 1560 |
| gagagggggca | ggcagctcct | tgcttatggg | tttccagagg | | | 1600 |

<210> SEQ ID NO 2
<211> LENGTH: 352
<212> TYPE: PRT
<213> ORGANISM: Rat

<400> SEQUENCE: 2

Met Asp Gly Pro Ser Asn Val Ser Leu Ile His Gly Asp Thr Thr Leu
1               5                   10                  15

Gly Leu Pro Glu Tyr Lys Val Val Ser Val Phe Leu Val Leu Leu Val
            20                  25                  30

Cys Thr Leu Gly Ile Val Gly Asn Ala Met Val Ile Leu Val Val Leu
        35                  40                  45

Thr Ser Arg Asp Met His Thr Pro Thr Asn Cys Tyr Leu Val Ser Leu
    50                  55                  60

Ala Leu Ala Asp Leu Leu Val Leu Leu Ala Ala Gly Leu Pro Asn Val

-continued

```
                65                  70                  75                  80
Ser Asp Ser Leu Val Gly His Trp Ile Tyr Gly Arg Ala Gly Cys Leu
                        85                  90                  95
Gly Ile Thr Tyr Phe Gln Tyr Leu Gly Ile Asn Val Ser Ser Phe Ser
            100                 105                 110
Ile Leu Ala Phe Thr Val Glu Arg Tyr Ile Ala Ile Cys His Pro Leu
        115                 120                 125
Arg Ala Gln Thr Val Cys Thr Val Ala Arg Ala Lys Arg Ile Met Ala
    130                 135                 140
Gly Ile Trp Gly Val Thr Ser Leu Tyr Cys Leu Leu Trp Phe Phe Leu
145                 150                 155                 160
Val Asp Leu Asn Val Arg Asp Asn Gln Arg Leu Glu Cys Gly Tyr Lys
                165                 170                 175
Val Pro Arg Gly Leu Tyr Leu Pro Ile Tyr Leu Leu Asp Phe Ala Val
            180                 185                 190
Phe Phe Ile Gly Pro Leu Leu Val Thr Leu Val Leu Tyr Gly Leu Ile
        195                 200                 205
Gly Arg Ile Leu Phe Gln Ser Pro Leu Ser Gln Glu Ala Trp Gln Lys
    210                 215                 220
Glu Arg Gln Pro His Gly Gln Ser Glu Ala Ala Pro Gly Asn Cys Ser
225                 230                 235                 240
Arg Ala Lys Ser Ser Arg Lys Gln Ala Thr Arg Met Leu Ala Val Val
                245                 250                 255
Val Leu Leu Phe Ala Val Leu Trp Thr Pro Tyr Arg Thr Leu Val Leu
            260                 265                 270
Leu Asn Ser Phe Ala Gln Pro Phe Leu Asp Pro Trp Val Leu Leu
        275                 280                 285
Phe Cys Arg Thr Cys Val Tyr Thr Asn Ser Ala Val Asn Pro Val Val
    290                 295                 300
Tyr Ser Leu Met Ser Gln Lys Phe Arg Ala Ala Phe Leu Lys Leu Cys
305                 310                 315                 320
Trp Cys Arg Ala Ala Gly Pro Gln Arg Arg Ala Ala Arg Val Leu Thr
                325                 330                 335
Ser Asn Tyr Ser Ala Ala Gln Glu Thr Ser Glu Gly Thr Glu Lys Met
            340                 345                 350
```

<210> SEQ ID NO 3
<211> LENGTH: 17
<212> TYPE: DNA
<213> ORGANISM: Artificial Sequence
<220> FEATURE:
<221> NAME/KEY: modified_base
<222> LOCATION: (9, 12)
<223> OTHER INFORMATION: i
<220> FEATURE:
<223> OTHER INFORMATION: Description of Artificial Sequence:synthetic
      primer

<400> SEQUENCE: 3
atyrsyrtng anmgrta                                                    17

<210> SEQ ID NO 4
<211> LENGTH: 20
<212> TYPE: DNA
<213> ORGANISM: Artificial Sequence
<220> FEATURE:
<221> NAME/KEY: modified_base
<222> LOCATION: (11, 14)
<223> OTHER INFORMATION: i

```
<220> FEATURE:
<223> OTHER INFORMATION: Description of Artificial Sequence:synthetic
      primer

<400> SEQUENCE: 4
mwggyrtaga nsanmggrtt                                                    20

<210> SEQ ID NO 5
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: PYRROLIDONE CARBOXYLIC ACID
<220> FEATURE:
<223> OTHER INFORMATION: Description of Artificial Sequence:synthetic
      peptide

<400> SEQUENCE: 5

Glu His Pro Gly
 1
```

THYROTROPIN-RELEASING HORMONE RECEPTOR 2(TRHR-2)

CROSS REFERENCE TO RELATED APPLICATIONS

The present application represents U.S. National stage of international application PCT/SE97/01999, which has an international filing date of Nov. 28, 1997, and which was published in English under Article 21(2) of the PCT on Jun. 11, 1998; The international application claims priority to Swedish Application 9604439-1, which was filed on Dec. 2, 1996.

FIELD OF THE INVENTION

The present invention is in the field of biological receptors and the various uses that can be made of such receptors. More specifically, it relates to nucleic acids encoding a novel receptor for thyrotropin-releasing hormone and to the receptor protein itself.

BACKGROUND OF THE INVENTION

Thyrotropin-releasing hormone (TRH) is a tripeptide (pyroglutamic acid-histidine-proline-amide) present in the central nervous system (thalamus, cerebral cortex, spinal cord) as well as in the periphery (pancreas, gastrointestinal tract, placenta). In the hypothalamus, TRH is synthesized by peptidergic neurons of supraoptic and paraventricular nuclei. It is then axonally transported to the median eminence where it is stored. Upon secretion into the bloodstream, TRH is transported to the pituitary where it stimulates the production of thyroid stimulating hormone (TSH) which, in turn, stimulates the production of thyroxin (T4) in the thyroid gland (Gaillard, in *Pharmacologie: Des Concepts Fondamentaux Aux Applications Thérapeutiques*, M. Shorderet ed., pp. 415–448 (1992)).

In addition to its role in regulating the synthesis and secretion of hormones from the anterior pituitary, there is evidence that TRH acts as a neurotransmitter (Wu, et al., *Neurosci. Let.* 142:143–146 (1992)). TRH is found abundantly in the central nervous system and exogenous administration of TRH elicits a variety of behavioral changes. It produces a rapid onset, neurotransmitter-like, excitation of spinal lower motor neurons and reduces neurological deficits observed after traumatic spinal cord injury in cats.

The distribution of TRH-containing cells, fibers or receptors suggests a potential role for TRH in the perception of noxious stimuli. Specifically, TRH is present in the periaqueducal gray (PAG), the nuclei raphe magnus (NMR), in the pallidus and dorsal horn of the spinal cord. TRH binding sites have been found in the brain, pituitary, dorsal and ventral horns of the spinal cord, and in peripheral tissues. When injected centrally (I.C.V. and I.C.), TRH induces a short lasting supraspinal antinociception. The analgesia induced by I.C.V. TRH injection is twice as great, on a molar basis, as that induced by morphine (Boschi, et al., *Br. J. Pharmacol.* 79:85–92 (1983)). This antinociceptive effect is detected in models of chemically and mechanically, but not thermally, induced pain.

The actions of TRH are mediated by the stimulation of specific cell surface receptors. There is evidence that TRH receptors found in the pituitary transmit their signal to the cell interior through a G protein to trigger the inositol phospholipid-calcium-protein kinase C transduction pathway (Straub, et al., *Proc. Nat'l. Acad. Sci. U.S.A.* 87:9514–9518 (1990); Duthie, et al., *Mol. Cell. Endocrinol.* 95:R11–R15 (1993)). A cDNA sequence encoding a G protein-coupled TRH receptor was first isolated from mouse pituitary cells using an expression cloning strategy (Straub, et al., *Proc. Nat'l. Acad. Sci. U.S.A.* 87:9514–9518 (1990)). Subsequently, several groups have described the cloning of rat TRH receptor cDNAs expressed in either a pituitary tumor cell line (GH3) or in pituitary gland (Duthie, et al., *Mol. Cell. Endocrinol.* 95:R11–R15 (1993); De La Pena, et al., *J. Biol. Chem.* 267:25703–25708 (1992)). In addition, two isoforms of the rat TRH receptor have been shown to be generated from a single gene by alternative splicing (De La Pena, et al., *J. Biol. Chem.* 267:25703–25708 (1992)).

In addition to receptors isolated from the mouse and rat, a human TRH receptor cDNA has been cloned by Matre et al. (*Biochem. Biophys. Res. Comm.* 195:179–185 (1993)). With the exception of its C-terminal region, the predicted amino acid sequence of the human receptor was found to be more than 95% homologous to its counterparts from the rat and mouse.

Using synthetic TRH analogues, a dissociation of endocrine and CNS effects has been observed, suggesting that subtypes of TRH receptor may exist. Certain analogues were found to affect sleeping time and breathing frequency in test animals even though they failed to bind to pituitary or brain receptors and had no measurable TSH release activity (Alexandrova, et al., *Gen. Physiol. Biophys.* 10:287–297 (1991)). Other analogues, modified in the C-terminal region, have been identified which are ineffective in treating traumatic spinal cord injury but which maintain the same endocrine effects as normal TRH (Faden, *Brain Research* 486:228–235 (1989)).

The existence of distinct TRH receptor subtypes has also been suggested by biochemical experiments. Specifically, TRH receptors isolated from the brain were found to have an isoelectric point of 5.5 whereas those isolated from the pituitary were found to have an isoelectric point of only 4.9. One possible explanation for this difference is that the receptors in the brain and those in the pituitary have different amino acid sequences (Burt, *Ann. NY Acad. Sci.* 553:188 (1989)). In addition, electrophysiological experiments and measurements of intracellular calcium concentration have suggested that TRH and TRH metabolites present in the brain may act by binding to different subtypes of TRH binding sites (Toledo-Aral, et al., *J. Physiol.* 472:327–340 (1993)).

Therapeutically, it is clear that agonists and antagonists of TRH binding have potential value in regulating endocrine function, controlling pain, and in the treatment of spinal cord injury. The ability to identify such agents will depend upon the availability of purified TRH receptors suitable for binding assays. Such assays could be used to screen for TRH agonists and antagonists; to determine the extent to which a patient's plasma contains an appropriate level of binding activity; and to help monitor the purity and effectiveness of agents at all stages of drug development.

SUMMARY OF THE INVENTION

To date, the only TRH receptor which has been cloned has been designated TRHR-1. The present invention is based upon the discovery of a new receptor for TRH which differs from TRHR-1 in terms of structure, tissue distribution and binding characteristics. Thus, in its first aspect, the invention is directed to a protein, except as existing in nature, comprising the amino acid sequence consisting functionally of the sequence of SEQ ID NO:2. The term "consisting functionally of" refers to proteins in which the sequence of SEQ ID NO:2 has undergone additions, deletions or substitutions which do not substantially alter the functional characteristics of the receptor. The term is intended to encompass proteins having exactly the same amino acid sequence as that of SEQ ID NO:2, as well as proteins with sequence differences that are not substantial as evidenced by their retaining the basic, qualitative ligand binding properties of TRHR-2.

The invention also encompasses substantially pure proteins with sequences consisting essentially of that of SEQ ID NO:2; antibodies that bind preferentially to such proteins (i.e., antibodies having at least a 100-fold greater affinity for TRHR-2 than any other protein); and antibodies made by a process involving the injection of a pharmaceutically acceptable preparation of TRHR-2 into an animal capable of antibody production. In a preferred embodiment, monoclonal antibody to TRHR-2 is produced by injecting the pharmaceutically acceptable preparation of TRHR-2 into a mouse and then fusing mouse spleen cells with myeloma cells.

The invention is also directed to a substantially pure polynucleotide encoding a protein comprising the amino acid sequence consisting functionally of SEQ ID NO:2. This aspect of the invention encompasses polynucleotides encoding proteins consisting essentially of the amino acid sequence of SEQ ID NO:2, expression vectors comprising such polynucleotides, and host cells transformed with such vectors. Also included is the recombinant TRHR-2 protein produced by host cells made in this manner. Preferably, the polynucleotide encoding TRHR-2 has the nucleotide sequence shown in SEQ ID NO:1, and the vectors and host cells used for expression of TRHR-2 also use this particular polynucleotide.

In another aspect, the present invention is directed to a method for assaying a test compound for its ability to bind to TRHR-2. This assay is performed by incubating a source of TRHR-2 with a ligand known to bind to the receptor and with the test compound. The source of TRHR-2 should be substantially free of other types of TRH receptors such as TRHR-1, e.g., greater than 90% of the TRH receptors present in the source should correspond to TRHR-2. Upon completion of incubation, the ability of the test compound to bind to TRHR-2 is determined by the extent to which ligand binding has been displaced. The preferred ligand is either TRH or TRH which has been labelled with a detectable compound. The preferred source of TRHR-2 for use in the assay is a cell transformed with a vector for expressing the receptor and comprising a polynucleotide encoding a protein consisting essentially of the amino acid sequence of SEQ ID NO:2. Instead of using cells in the assay, a membrane preparation can be prepared from the cells and this can be used as a source of TRHR-2. Although not essential, the assay can be accompanied by a determination of changes in a second messenger, e.g. changes in the intracellular concentration of calcium. This should help to determine whether a test compound or analogue that binds to TRHR-2 is acting as an agonist or antagonist of TRH.

In another aspect, the present invention is directed to a method for assaying a test compound for its ability to alter the expression of the TRHR-2 gene. This method is performed by growing cells expressing TRHR-2, but substantially free of other TRH receptors, in the presence of the test compound. Cells are then collected and the expression of TRHR-2 is compared with expression of control cells grown under essentially identical conditions but in the absence of the test compound. In a preferred embodiment, the cells expressing TRHR-2 are cells transformed with an expression vector comprising a polynucleotide sequence encoding a protein consisting essentially of the amino acid sequence of SEQ ID NO:2. A preferred test compound is an oligonucleotide at least 15 nucleotides in length and comprising a sequence complimentary to a sequence shown in SEQ ID NO:1. The preferred method for determining receptor expression is by means of a receptor binding assay.

Definitions

The description that follows uses a number of terms that refer to recombinant DNA technology. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain a marker suitable for use in the identification of transformed cells. For example, markers may provide tetracycline resistance or ampicillin resistance.

Expression vector: A vector similar to a cloning vector but which is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

Substantially pure: As used herein, "substantially pure" means that the desired product is essentially free from contaminating cellular components. Contaminants may include, but are not limited to, proteins, carbohydrates or lipids. One method for determining the purity of a protein or nucleic acid is by electrophoresing a preparation in a matrix such as polyacrylamide or agarose. Purity is evidenced by the appearance of a single band after staining.

Host: Any prokaryotic or eukaryotic cell that is the recipient of a replicable expression vector or cloning vector is the "host" for that vector. The term encompasses prokaryotic or eukaryotic cells that have been engineered to incorporate a desired gene on its chromosome or in its genome. Examples of cells that can serve as hosts are well known in the art, as are techniques for cellular transformation (see e.g. Sambrook et al., Molecular Cloning: A Laboratory Manual, 2nd ed. Cold Spring Harbor (1989)).

Promoter: A DNA sequence typically found in the 5' region of a gene, located proximal to the start codon. Transcription is initiated at the promoter. If the promoter is of the inducible type, then the rate of transcription increases in response to an inducing agent.

Complementary Nucleotide Sequence: A complementary nucleotide sequence, as used herein, refers to the sequence that would arise by normal base pairing. For example, the nucleotide sequence 5'-AGAC-3' would have the complementary sequence 5'-GTCT-3'.

Expression: Expression is the process by which a polypeptide is produced from DNA. The process involves the transcription of the gene into mRNA and the translation of this mRNA into a polypeptide.

DETAILED DESCRIPTION OF THE INVENTION

The present invention is directed to the TRHR-2 receptor protein, genetic sequences coding for the receptor, a method for assaying compounds for their ability to bind to TRHR-2 and a method for assaying compounds for their ability to alter TRHR-2 expression. The receptor and the nucleic acids encoding the receptor may be distinguished from all known TRH receptors based upon structure, tissue distribution and binding characteristics. With respect to structure, the relationship between TRHR-2 and other TRH binders is shown in FIG. 2. The greatest homology was observed between TRHR-2 and the human TRHR-1 receptor. In transmembrane regions, the sequence homology between these receptors ranged from 52% to 80%. The alignment of TRHR-2 relative to other G protein-coupled receptors, or other members of the neuropeptide receptor subfamily, indicates a unique sequence indicative of a newly characterized receptor.

It will be understood that the present invention encompasses not only the sequence identical to that shown in FIG. 1, but also sequences that are essentially the same and which produce a receptor retaining the basic binding characteristics of TRHR-2. Thus, the invention relates to proteins comprising amino acid sequences consisting functionally of the sequence of SEQ ID NO:2. In this regard, it is well known that techniques such as site-directed mutagenesis may be used to introduce variations in a protein structure. Variations in TRHR-2 introduced by this or some similar method are encompassed by the invention to the extent that such variant receptors retain the ability to preferentially bind to TRH or TRH-like peptides.

The TRHR-2 receptor may also be distinguished from similar proteins based upon its binding characteristics. pGlu-His-Pro-Gly does not show any binding to GH4C1 cells but displays a Ki value of 640 nM to the TRHR-2 receptor. This suggests that TRHR-2 is less susceptible than TRHR-1 to C-terminal modification of the ligand.

In addition, TRHR-2 may be distinguished from other receptors for TRH based upon its tissue distribution. In situ hybridization studies performed on the rat have indicated a distinct distribution of TRHR-2 in the pituitary gland, spinal cord, and brain. In the pituitary gland, moderate levels of TRHR-1 mRNA have been observed throughout the anterior lobe whereas both the posterior and intermediate lobes appear to be devoid of expression. In contrast, no specific hybridization signal was detected for TRHR-2 in the pituitary.

In the CNS, TRHR-2 mRNA is distributed throughout the entire dorsal horn of the spinal cord whereas TRHR-1 is located in sparsely distributed neurons of the ventral horn (Zabavnik, et al., *Neuroscience* 53:877–887 (1993)). This is consistent with experiments in which autoradiography was used to detect $^3$H-TRH binding sites and which suggest that TRH receptors are expressed in both the dorsal and ventral horns of the spinal cord (Manaker, et al., *J. Neurosci.* 5:167–174 (1985)). In the brain, it appears that TRHR-2 mRNA is present in much higher levels than the mRNA for TRHR- 1. In particular, TRHR-1 mRNA expression was observed only at very low levels in the piriform cortex, amygdala and discreet hypothalamic nuclei (superchiasmatic nucleus, SCN; ventromedial hypothalamic nucleus, VMH; paraventricular hypothalamic nucleus, PVN; and anterior hypothalamic area posterior part, AHP). In no case, with the possible exception of the amygdala, was TRHR-1 mRNA detected in regions enriched in TRHR-2 such as the thalamus, medial habenular nucleus, frontal and parietal cortices, the pontine nucleus, or the cerebellum.

The pattern of TRHR-2 expression within the rat CNS suggests the involvement of at least two distinct modalities: somatosensory (possibly including pain transmission) and motor. The restricted localization of TRHR-2 mRNA throughout the entire dorsal horn of the spinal cord, reticular formation and somatosensory nuclei of the thalamus (VPL, VPM) is consistent with ascending pathways such as the spinothalamic and trigeminothalamic tracts (pain and crude touch) as well as the medial lemniscal system (discriminative touch). The presence of high levels of TRHR-2 restricted to the pontine nucleus and the cerebellum is consistent with a role in motor control and/or proprioception. These receptors may also be the anatomical substrate for the previously described TRH effects on motor control (see Engle, et al., *The Lancet* 83841:73–75 (1983)). To date, only very low levels of TRH peptide or TRH binding sites have been reported in the cerebellum suggesting that an alternate ligand, as yet unidentified, may also bind to this receptor.

I. Nucleic Acids Coding for TRHR-2

As discussed above, DNA sequences coding for TRHR-2 are expressed in a variety of tissues, any of which may serve as a source for the isolation of nucleic acid coding for the receptor. The preferred source is the spinal cord of the rat, but spinal cord tissue from other species may be used as well. In addition, cells or cell lines expressing TRHR-2 may serve as a source for nucleic acid. These may either be cultured cells that have not undergone transformation or cell lines specifically engineered to express recombinant TRHR-2.

Many methods are available for isolating DNA sequences and may be adapted for the isolation of TRHR-2 nucleic acid (see for example Sambrook, et al., *Molecular Cloning: A Laboratory Manual,* 2nd ed., Cold Spring Harbor Press (1989)). As discussed in the Examples, a preferred method of isolation is to use reverse transcription PCR on mRNA isolated from rat spinal cord to produce probes and to then use these probes to screen a cDNA library. The preferred primers for carrying out the PCR amplification are:

TM3-4: 5'-AT(C or T)(A or G)(C or G)(C or T)(A or G)TIGAI(A or C)G(A or G)TA-3' (SEQ ID NO:3)

TM7-4: 5'-(A or C)(A or T)GG(C or T)(A or G)TAGAI(C or G)AI(A or C)GG(A or G)TT-3' (SEQ ID NO:4)

After having produced cDNA by reverse transcription, the above primers are used for amplification. This should result in partial amplification of the THRH2 cDNA and produce fragments suitable for screening cDNA libraries.

Although the procedure above is known to be suitable for obtaining TRHR-2 nucleic acid, it is expected that alternative techniques can be developed with relatively little effort. Thus, cDNA libraries may be screened using probes synthesized based upon the TRHR-2 sequence shown in FIG. 1. In general, probes should be at least 14 nucleotides long and should not be selected from regions known to be highly conserved among proteins, e.g., the transmembrane domains of G-protein linked receptors. Alternatively, using the sequence shown in FIG. 1, it should be possible to select different PCR primers and amplify the full length TRHR-2 sequence. The same techniques that have proven successful in the rat can be used to obtain TRHR-2 sequences from other species, e.g., from cells or tissues derived from humans.

II. Production and Isolation of TRHR-2 Recombinant Protein

In order to express recombinant TRHR-2, a DNA encoding the structural sequence for the protein described above must be placed in a vector containing transcriptional and translational signals recognizable by an appropriate host. The cloned TRHR-2 sequences, preferably in double-stranded form, are inserted into the expression vector in operable linkage, i.e., they are positioned so as to be under the control of the vector's regulatory sequences and in such a manner that mRNA is produced that is translated into the TRHR-2 amino acid sequence.

Expression of the TRHR-2 receptor protein in different hosts may result in different post-translational modifications that can, potentially, alter the properties of the receptor. Preferably, nucleic acid encoding TRHR-2 is expressed in eukaryotic cells, especially mammalian cells. These cells provide post-translational modifications which, inter alia, aid in the correct folding of the receptor protein. An appropriate vector, pCDNA3-THR2, and host, HEK293 cells, are described under "Examples."

Other mammalian cells that may be used include, without limitation, NIH-3T3 cells, CHO cells, HeLa cells, LM(tk⁻) cells, etc. Vectors suitable for use in each of the various cell types are well known in the art (see e.g., Sambrook, et al., supra). Preferred eukaryotic promoters include that of the mouse metallothionein I gene; the TK promoter of Herpes virus; the SV40 early promoter; and the yeast GAL4 gene promoter. Some examples of suitable prokaryotic promoters include those capable of recognizing T4 polymerases, the $P_R$ and $P_L$ promoters of bacteriophage lambda, and the trp, recA, heat shock and lacZ promoters of *E coli*. Expression vectors may be introduced into host cells by methods such as calcium phosphate precipitation, microinjection or electroporation. Cells expressing the TRHR-2 receptor can be selected using methods well known in the art. One simple method for confirming the presence of the receptor nucleic acid in cells is to perform PCR amplification using the procedures and primers discussed above. The presence of functional receptor may be confirmed by performing binding assays using labelled TRH.

Once cells producing recombinant TRHR-2 receptor have been identified, they may be used in either binding assays or in assays designed to identify agents capable of altering TRHR-2 expression. Alternatively, membranes may be isolated from the cells and these may be used in receptor binding assays.

III. Antibodies to TRHR-2

The present invention is also directed to antibodies that bind preferentially to TRHR-2 and to a process for producing such antibodies. Antibodies that "bind specifically to TRHR-2" are defined as those that have at least a 100-fold greater affinity for TRHR-2 than for any other protein, including TRHR-1. The process for producing such antibodies may involve either injecting the TRHR-2 protein itself into an appropriate animal or, preferably, injecting short peptides made to correspond to different regions of TRHR-2. The peptides should be at least five amino acids in length and should be selected from regions believed to be unique to the TRHR-2 protein. Thus, highly conserved transmembrane regions should generally be avoided in selecting peptides for the generation of antibodies.

Methods for making and detecting antibodies are well known to those of skill in the art as evidenced by standard reference works such as: Harlow, et al., *Antibodies: A Laboratory Manual*, Cold Spring Harbor Laboratory, N.Y. (1988); Klein, *Immunology: The Science of Self-Nonself Discrimination* (1982); Kennett, et al., *Monoclonal Antibodies and Hybridomas: A New Dimension in Biological Analyses* (1980); and Campbell, "Monoclonal Antibody Technology," in *Laboratory Techniques in Biochemistry and Molecular Biology* (1984)).

"Antibody," as used herein, is meant to include intact molecules as well as fragments which retain their ability to bind to antigens (e.g., Fab and F(ab')₂ fragments). These fragments are typically produced by proteolytically cleaving intact antibodies using enzymes such as papain (to produce Fab fragments) or pepsin (to produce F(ab')₂ fragments). The term "antibody" also refers to both monoclonal and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al. in *Monoclonal Antibodies and T-Cell Hybridomas, Elsevier, N.Y., pp.* 563–681 (1981)). In general, this technology involves immunizing an animal, usually a mouse, with either intact TRHR-2 or a fragment derived from TRHR-2. The splenocytes of the immunized animals are extracted and fused with suitable myeloma cells, e.g., $SP_2O$ cells. After fusion, the resulting hybridoma cells are selectively maintained in HAT medium and then cloned by limiting dilution (Wands, et al., *Gastroenterology* 80:225–232 (1981)). The cells obtained through such selection are then assayed to identify clones which secrete antibodies capable of binding TRHR-2.

The antibodies, or fragments of antibodies, of the present invention may be used to detect the presence of TRHR-2 protein using any of a variety of immunoassays. For example, the antibodies may be used in radioimmunoassays or immunometric assays, also known as "two-site" or "sandwich" assays (see Chard, T., "An Introduction to Radioimmune Assay and Related Techniques," in *Laboratory Techniques in Biochemistry and Molecular Biology,* North Holland Publishing Company, N.Y. (1978)). In a typical immunometric assay, a quantity of unlabelled antibody is bound to a solid support that is insoluble in the is fluid being tested, e.g., blood, lymph, cellular extracts, etc. After the initial binding of antigen to immobilized antibody, a quantity of detectably labelled second antibody (which may or may not be the same as the first) is added to permit detection and/or quantitation of bound antigen (see e.g. *Radioimmune Assay Method,* Kirkham, et al., ed. pp. 199–206 (E&S. Livingstone, Edinburgh (1970)). Many variations of these types of assays are known in the art and may be employed for the detection of TRHR-2.

Antibodies to TRHR-2 may also be used in the purification of either the intact receptor or fragments of the receptor (see generally, Dean, et al., *Affinity Chromatography, A Practical Approach,* IRL Press (1986)). Typically, antibody is immobilized on a chromatographic matrix such as Sepharose 4B. The matrix is then placed in a column and the preparation containing TRHR-2 is passed through under conditions that promote binding, e.g., under conditions of low salt. The column is then washed and bound TRHR-2 is eluted using a buffer that promotes dissociation from antibody, e.g., buffer having an altered pH or salt concentration. The eluted TRHR-2 may then be transferred into a buffer of choice, e.g., by dialysis, and either stored or used directly.

IV. Assay for TRHR-2 Binding

One of the main uses for TRHR-2 nucleic acids and recombinant proteins is in assays designed to identify agents, other than TRH, capable of binding to the TRHR-2 receptor. Such agents may either be agonists, mimicking the effects of TRH, or antagonists, inhibiting the effects of TRH. Of particular interest is the identification of agents which bind to TRHR-2 receptors and increase the intracellular concentration of calcium in the cells. These agents have potential therapeutic application as analgesics; anesthetics; for reducing the damage due to spinal trauma; for controlling endocrine function; and for regulating gastric secretion, particularly in the treatment of ulcers.

An example of an assay that may be used for detecting compounds binding to TRHR-2 is presented in the examples and typical binding curves that may be obtained are shown in FIG. 4. The essential feature of the assays is that a source of TRHR-2 is incubated together with a ligand known to bind to the receptor and with a compound being tested for binding activity. The preferred source for TRHR-2 is cells, preferably mammalian cells, transformed recombinantly to express the receptor. The cells selected should not express a substantial amount of any other receptor which binds TRH, e.g., TRHR-1. This can easily be determined by performing TRH binding assays on cells derived from the same tissue or cell lines as those recombinantly expressing TRHR-2 but which have not undergone transformation.

The assay may be performed either with intact cells or, alternatively, with membranes prepared from the cells (see e.g., Wang, et al., *Proc. Natl. Acad Sci. USA* 90:10230–10234 (1993)). The membranes are incubated with a ligand specific for TRHR-2 and with a preparation of the compound being tested. After binding is complete, receptor is separated from the solution containing ligand and test compound, e.g., by filtration, and the amount of binding that has occurred is determined. Preferably, the ligand used is TRH detectably labelled with a radioisotope. However, fluorescent or chemiluminescent labels can be used instead. Among the most commonly used fluorescent labelling compounds are fluorescein, isothiocynate, rhodamine, phycoerythrin, phycocycanin, allophycocyanin, o-phthaldehyde and fluorescamine. Useful chemiluminescent compounds include luminol, isoluminol, theromatic acridinium ester, imidazole, acridinium salt, and oxalate ester. Any of these agents which can be used to detectably label TRH will produce a ligand suitable for use in the assay.

Nonspecific binding may be determined by carrying out the binding reaction in the presence of a large excess of unlabelled ligand. For example, labelled TRH may be incubated with receptor and test compound in the presence of a thousandfold excess of unlabelled TRH. Nonspecific binding should be subtracted from total binding, i.e., binding in the absence of unlabelled TRH, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of tests compound is compared with that obtained in the presence of labelled ligand alone to determine the extent to which the test compound has displaced TRH.

In performing binding assays, care must be taken to avoid artifacts which may make it appear that a test compound is interacting with the TRHR-2 receptor when, in fact, binding is being inhibited by some other mechanism. For example, the compound being tested should be in a buffer which does not itself substantially inhibit the binding of TRH to TRHR-2 and should preferably be tested at several different concentrations. Preparations of test compound should also be examined for proteolytic activity, and it is desirable that antiproteases be included in assays. Finally, it is desirable that compounds identified as displacing the binding of ligand to TRHR-2 receptor be re-examined in a concentration range sufficient to perform a Scathard analysis on the results. This type of analysis is well known in the art and can be used for determining the affinity of a test compound for receptor (see e.g., Ausubel, et al., *Current Protocols in Molecular Biology*, 11.2.1–11.2.19 (1993); *Laboratory Techniques in Biochemistry and Molecular Biology*, Work, et al., ed., N.Y. (1978), etc.). Computer programs may be used to help in the analysis of results (see e.g., Manson, Methods Enzymol. 92:543–577 (1983); McPherson, *Kinetic, EBDA Ligand, Lowry-A Collection of Radioligand Binding Analysis Programs,* Elsevier-Biosoft, U.K. (1985)).

Assays for determining changes in second messenger, e.g. changes in intracellular calcium concentration, may be performed using compounds that have been identified as a result of their ability to bind to TRHR-2. These assays may be carried out as discussed in the examples or using other methods for determining intracellular calcium concentration. Typically, calcium concentration assays will be performed separately from binding assays, but it may also be possible to perform binding and calcium concentration assays on a single preparation of cells. TRHR-2 binding compounds that stimulate an increase in intracellular calcium in cells are agonists of TRH and should mimic its biological effects. In contrast, compounds that specifically bind to TRHR-2 receptors but which do not increase intracellular calcium are antagonists of TRH and should inhibit its biological effects.

V. Assay for Ability to Modulate TRHR-2 Expression

One way to either increase or decrease the biological effects of TRH is to alter the extent to which TRHR-2 is expressed in cells. Therefore, assays for the identification of compounds that either inhibit or enhance expression of TRHR-2 are of considerable interest. These assays are carried out by growing cells expressing TRHR-2 in the presence of a test compound and then comparing receptor expression in these cells with cells grown under essentially identical condition but in the absence of the test compound. As in the binding assays discussed above, it is desirable that the cells used be substantially free of receptors for TRH other than TRHR-2. Scatchard analysis of binding assays performed with detectably labelled TRH can be used to determine receptor number.

The binding assays may be carried out as discussed above in section IV and will preferably utilize cells that have been engineered to recombinantly express TRHR-2 as described in sections I and II. Ideally, the expression of TRHR-2 protein is controlled by the naturally occurring TRHR-2 regulatory element, e.g., the promoter which regulates cellular TRHR-2 expression in vivo.

A preferred group of test compounds for inclusion in the TRHR-2 expression assay consists of oligonucleotides complimentary to various segments of the TRHR-2 nucleic acid sequence. These oligonucleotides should be at least 15 bases in length and should be derived from non-conserved regions of the receptor nucleic acid sequence.

Oligonucleotides which are found to reduce receptor expression may be derivatized or conjugated in order to increase their effectiveness. For example, nucleoside phosphoro-thioates may be substituted for their natural counterparts (see Cohen, *Oligodeoxynucleotides, Antisense Inhibitors of Gene Expression,* CRC Press (1989)). The oligonucleotides may be delivered to a patient in vivo for the purpose of inhibiting TRHR-2 expression. When this is done, it is preferred that the oligonucleotide be administered in a form that enhances its uptake by cells. For example, the oligonucleotide may be delivered by means of liposome or conjugated to a peptide that is ingested by cells (see e.g., U.S. Pat. Nos. 4,897,355 and 4,394,448; see also non-U.S. patent documents WO 89/03849 and EP0263740). Other methods for enhancing the efficiency of oligonucleotide delivery are well known in the art and are also compatible with the present invention.

Having now described the invention, the same will be more readily understood through reference to the following examples which are provided by way of illustration and which are not intended to limit the scope of the invention.

EXAMPLES

Example 1
Cloning and Sequencing of a Rat (TRHR-2) Thyrotropin-Releasing Hormone Receptor
A. Cloning and Sequencing Procedures In order to isolate novel cDNA sequences encoding G protein-coupled receptors, a PCR-based homology screening strategy was used. Rat spinal cord mRNA was isolated using the FastTrack™ kit (InVitrogen, San Diego, Calif.). Candidate sequences likely to encode G protein-coupled receptors were amplified from this mRNA by reverse transcription PCR using the following primers:

TM3-4: 5'-AT(C or T)(A or G)(C or G)(C or T)(A or G)TIGAI(A or C)G(A or G)TA-3' (SEQ ID NO:3)
TM7-4: 5'-(A or C)(A or T)GG(C or T)(A or G)TAGAI(C or G)AI(A or C)GG(A or G)TT-3' (SEQ ID NO:4)

The templates for PCR amplification were synthesized using GeneAmp RNA PCR kits (N808-0017 Perkin Elmer) together with 200 ng of spinal cord poly A$^+$ RNA. One aliquot of the produced cDNA was then amplified with 200 pmoles each of TM3-4 and TM7-4 primers and 2.5 units of Taq DNA polymerase in 50 mM KCl, 1.5 mM MgCl$_2$, 10 mM Tris(HCl), 200 µM dNTPs, pH 9.0. The reaction tubes were heated at 95 degrees C. for one minute and subjected to 39 cycles of denaturation (95 degrees C./min), annealing (42 degrees C./min) and extension (72 degrees C./min).

The amplified fragments were analyzed and size fractionated on a 1% agarose gel. Fragments between 500 bp and 800 bp were excised from the gel, purified using the Sephaglas BandPrep™ kit from Pharmacia (cat# 27-9285-01), and inserted into the pGEM-T vector from Promega (cat# A3600). Recombinant pGEM-T clones were selected randomly and plasmid DNA was prepared using the alkaline lysis method starting with 10 ml of bacterial culture. The DNA sequence from these clones was determined using the Sanger dideoxynucleotide chain termination method on denatured double-stranded plasmid templates (Sanger et al., *Proc. Natl. Acad. Sci. USA* 74:5463–5437 (1977)), using the T7 sequencing kit from Pharmacia (cat# 27-1682-01). The clone pGemT-1-75 showed marked sequence homologies with known GPCRs. The most homologous sequence was the human and rat thyrotropin release hormone receptors (TRHR) (Matre et al., *Biochem. Biophys. Res. Comm.* 195:179–185 (1993); Hinuma et al., *Bioch. Biophys. Acta* 1219:251–259 (1994); Duthie et al., *Mol Cell. Endocrinol.* 95:R11–R15 (1993)), although a perfect match was not identified.

The insert DNA fragment of clone pGemT-1-75 was excised from the vector using Pst I and Sac II, isolated from an agarose gel and labeled with $^{32}$P by random primed synthesis using the Ready-To-Go™ DNA labeling kit (27-9251-01) from Pharmacia (Sambrook et al., *Molecular Cloning: A Laboratory Manual,* Cold Spring Harbor Laboratory (2nd ed. 1989)). This probe was used to screen a rat brain stem-spinal cord cDNA library in λ ZAP II (Stratagene, cat# 936521). The filters were incubated with the probe for 18 hours at 65° C. in 2×SSC, 5×Denhardt's solutions and 0.2% SDS. The filters were rinsed twice in 0.1×SSC, 0.2% SDS at room temperature. They were then washed twice for 45 min in 0.1×SSC, 0.2% SDS at 65° C., once for 45 min at 65° C. in 5 mM EDTA, 0.2% SDS, pH 8.0 and finally using 0.1×SSC at room temperature.

Hybridization-positive phages were purified and their inserts rescued by helper phage mediated excision to yield plasmid DNA (Murray et al., *Mol. Gen. Genet.* 150:53–61 (1977); Schweinfest et al., *Genet. Anal. Tech. Appl.* 7:64–70 (1990)). The insert of plasmid pBS/TRHR2 was sequenced after having generated a series of overlapping clones using the Erase-A-Base kit from Promega (cat# 65740).

B. Results

An open reading frame of 352 amino acids was detected flanked by 3' and 5' untranslated regions of, respectively, 183 and 361 bp. The sequence of the open reading frame is displayed in FIG. 1. The relative molecular mass of the predicted protein is 39,500 daltons. Hydropathy analysis of the encoded protein is consistent with a topography of seven transmembrane domains indicative of the G protein-coupled receptor family (Sprengel et al., "Hormone Receptors," in *Handbook of Receptors and Channels: G Protein-Coupled Receptors,* pp. 153–207, CRC Press (1994)). In addition, sequence analysis revealed that the open reading frame of clone pBS-TRHR2 contains several conserved structural features found among the members of the neuropeptide receptor family, including: an asparagine in TM1 (Asn40); a leucine (Leu64) and an aspartic acid (Asp 68) in TM2; and a serine (Ser109), an arginine (Arg120) and a tyrosine residue (Tyr121) in TM3. Other features of this TRHR-2 receptor gene are the presence of a potential site for N-glycosylation in the amino terminus (Asn6) and the presence of several serines and threonines in the carboxyl terminus and third intracellular loop, which may serve as potential sites for phosphorylation by protein kinases.

The overall sequence homology between TRHR-2 and the known rat TRH receptor is 50.6%. However the sequence homology is higher in the putative transmembrane domains. Respectively, the homologies between the known rat TRH receptor (TRHR-1) and TRHR-2 in TM1 to TM7 are 61%, 80%, 74%, 58%, 52%, 77% and 71%.

Example 2
Transient Transfection Experiments

To generate a mammalian expression vector, a 1.3 Kb StuI-Xbal restriction fragment, from pBS/TRHR2 was isolated and subcloned between the Xba I and Eco RV sites of pCDNA3 (InVitrogen, San Diego, Calif.). This expression vector was called pCDNA3-TRHR2. Plasmid DNA for further analysis was prepared using the Qiaprep system from Qiagen.

HEK293s cells were obtained form the Cold Spring Harbor laboratory. They were inoculated in 6-well plates (4×10$^5$ cells per well) or in 10 cm Petri dishes (2×10$^6$ cells per dish) in Dulbeco's Modified Essential Medium (DMEM, Gibco BRL, cat# 11995-032) supplemented with 10% fetal bovine serum (FBS), 100 U/ml penicillin, 100 µg/ml streptomycin and 0.25 µg/ml fungizone. One day after inoculation, the cells were transiently transfected using a modified CaCl$_2$ method. Three and a half mg of plasmid DNA per well or 20 µg per 10 cm petri dish was used. The cells were harvested 48 hours post transfection for ligand binding or signal transduction experiments. When transfected into HEK293 cells, pCDNA3-TRHR2 generated the expression of specific $^3$H-TRH binding sites. No specific $^3$H-TRH binding sites were generated by the transfection of the vector itself or a control pCDNA3 expression construct encoding an opioid receptor.

Example 3
Radioligand Binding to Stably Transfected Cells
A. Binding Assays

The TRH binding assay was performed on whole cells. Transfected cells were washed twice with HBSS (Gibco BRL, cat# 14065) supplemented with 0.05% bovine serum albumin, detached by gentle pipetting and aliquoted in eppendorf tubes for binding assays. One twentieth of the cells collected from a confluent 75 cm² flask was used per assay point. The binding reaction was performed in a total volume of 300 ml of binding buffer (HBSS+0.05% bovine serum albumin) containing the transfected cells and 10 nM of ³H-thyrotropin releasing hormone (Peninsula Laboratories Inc, cat # 7501) with or without unlabelled competitors. Non-specific binding was estimated in the presence of 1 mM of unlabelled TRH. Reactions were carried out for 60 min at room temperature and reactions were stopped by filtration through Unifilters-96 GF/B filters (Canberra Packard cat # 6005177) using the 96-well Filtermat 196 filtration system from Canberra Packard. The filters were washed 3 times with 1 ml of washing buffer (50 mM Tris(HCl), 3 mM $MgCl_2$, pH 7.0). They were then dried at 55° C. for one hour and 50 µl of mScint-20 (Canberra Packard) was added per well. Filters were counted with the Topcount microplate counter from Canberra Packard.

B. Production of Stably Transfected Cells

HEK293s cells in a 10 cm petri dish were transfected with 20 mg pCDNA3-TRHR2. After 14 days of selection in culture medium containing 600 µg/ml G418, resistant colonies were pooled. Then, single clones were purified by 2 rounds of limited dilution in 96 well plates. Clones of HEK293s cells expressing different levels of TRHR-2 receptor were selected using a 3H-TRH binding assay.

C. Results

A binding reaction was performed using HEK 293 cells expressing TRHR-2. A single class of saturable ³H-TRH binding site was detected displaying an estimated Kd for ³H-TRH of 2.5 nM and a $B_{max}$ of 430 fmol/mg proteins. Various TRH-related peptides were used in competition experiments. These experiments were performed using ³H-TRH as a tracer and revealed $IC_{50}$ values of 2.2 nM for pGlu-3 methyl-His-Pro-amide, 8.3 nM for TRH, 640 nM for pGlu-His-Pro-Gly, and >10000 nM for pGlu-Glu-Pro-amide (Table 1).

TABLE 1

Binding Parameters of TRH Receptors*

|  | 293S/TRH-R clonal cell line | GH4Cl Cells |
|---|---|---|
| $B_{MAX}$ (fmol/mg) | 534.56 ± 70.82 | 577.48 ± 80.77 |
| Kd (nM): ³H-TRH | 6.17 ± 1.51 | 5.32 ± 1.63 |
| $IC_{50}$ (nM): TRH (pGlu-His-Pro-amide) | 8.39 ± 2.31 | 5.33 ± 2.81 |
| $IC_{50}$ (nM): pGlu-Glu-Pro-amide | >>10000 | >>10000 |
| $IC_{50}$ (nM): pGlu-His-Pro-Gly | 640.67 ± 75.19 | >>10000 |
| $IC_{50}$ (nM): pGlu-3-methyl-His-Pro-amide | 2.20 ± 0.71 | 0.43 ± 0.27 |

*Three independent experiments were performed, each with duplicate data points.

Example 4

Functional Assay: Intracellular Calcium Mobilization

A. Assay Procedure

Intracellular calcium concentration changes where determined by fluorescence measurement of the intracellular, calcium-sensitive indicator Fura 2. Briefly, HEK293s cells were grown on glass cover slips in culture medium at 37° C., 5% $CO_2$ and diluted 10 fold every 3 days. The cells were loaded at room temperature for 30 min using 2 mM of is Fura 2/AM in simplified Grace's solution (SGS buffer) physiological buffer (NBS: 135 mM NaCl, 5 mM KCl, 1.8 mM $CaCl_2$, 1.2 mM $MgSO_4$, 10 mM HEPES, pH 7.4). Fura 2/AM is a membrane permeant, calcium-insensitive ester of Fura 2. After three washes in Fura-2 /AM-free buffer, the cells were incubated for 15 to 30 min in SGNBS at room temperature to insure full hydrolysis of the Fura 2 ester. The calcium-sensitive, hydrolyzed form of Fura 2 remains trapped intracellularly. Experiments were conducted at room temperature on single cells or small groups of 3 to 7 cells in a coverslip holder fitted to the stage of an IMT-2 inverted microscope equipped with a 40x-epifluorescence objective (UVFL40, 0.85, Olympus Optical Co, Tokyo) and coupled to a PTI ratio fluorescence system (Photon Technology International, London, Ontario, Canada). Sample illumination was provided by a 75 W xenon light source attached to a filter-based light chopper unit which provided 340 and 380 nm excitation wavelength alternating at a frequency of 5 Hz. The emitted light was passed through an adjustable rectangular aperture followed by a 505 nm interference filter (10-nm bandwidth), and its intensity was recorded by a photon counter detector. Dye leakage, as determined by loss of fluorescence over a period of 30 min, was undetectable at both excitation wavelengths.

The ratio of the fluorescence intensity at the two excitation wavelengths can be converted into an estimate of ionized intracellular calcium concentration by use of the formula: $[Ca^{2+}]_i = Kd \times (Fmin/Fmax) \times (R-Rmin)/(Rmax-R)$, where R, Rmin, and Rmax are the fluorescence ratios recorded during the experiment (R) and during calibration tests on unlysed cells using 4 mM ionomycin in SGNBS (Rmax), followed by 10 mM EGTA addition at pH 8.2 (Rmin). Fmin and Fmax are the corresponding fluorescence intensities for the 380 nm excitation and Kd is the Fura-2 dissociation constant at room temperature (135 nM).

Small volumes (10–50 µl) of drugs (hormones, agonists, neurotransmitters, TRH, bradykinin) from prediluted stock solutions prepared in the appropriate buffer solutions were directly added to the experimental chamber.

B. Results

Exposure of HEK293/TRHR-2 cells, but not wild type HEK 293 cells, to nanomolar concentrations of TRH resulted in a marked transient increase in the intracellular calcium concentration. The peak of $[Ca^{++}]_i$ concentration was reached after about 1 second and the baseline $[Ca^{++}]_i$ was attained after about 1 minute. TRH did not require the presence of extracellular calcium to evoke the transient raise in $[Ca^{++}]_i$.

Example 5

Northern Blot Analysis

A rat Multiple Tissue Northern blot (Clonetech (cat# 7764-1) was used to study the distribution of TRHR-2 in various tissues. The blot contained 2 mg of rat poly(A)⁺ mRNA isolated from heart, brain, spleen, lung, liver, skeletal muscle, kidney and testes. The blot was first pre-hybridized at 42° C. for three hours in a solution containing 50% formamide, 5×SSPE, 10×Denhardt's solution, 100 µg/ml sheared and denatured salmon sperm DNA and 2% SDS. A radiolabelled probe was prepared using Ready-to-go DNA labelling kit (Pharmacia Biotech Cat.#27-9251-01) and the full length cDNA of the TRHR-2. Hybridization was carried out at 42° C. for about 18 hours in the solution described above. After an overnight hybridization, the blot was rinsed 2 times in 2×SSC, 0.05% SDS at room temperature and then washed 2 times for 15 minutes at room temperature followed by 2 washes at 50° C. for 15 minutes each and then 2 washes at 60° C. in the same solution. The blot was then exposed at −80° C. for 7 days to Kodak Biomax film with intensifying screens.

Expression of TRHR-2 mRNA was detected only in brain tissue. The apparent size of the mRNA is about 8 kb kilobases. Other tissues contained either no message or, at least, an insufficient amount of message to be detected after one week exposure under the conditions described.

Example 6
In Situ Hybridization
A. Hybridization Procedure
Animals and Tissue Preparation Adult male Sprague-Dawley rats (~300 gm; Charles River, St-Constant, Quebec) were sacrificed by decapitation. Brain, pituitary and spinal cord were promptly removed, snap-frozen in isopentane at −40° C. for 20 seconds and stored at −80° C. Frozen tissue was sectioned at 14 mm in a Microm HM 500 M cryostat (Germany) and thaw-mounted onto ProbeOn Plus slides (Fisher Scientific, Montreal, Quebec). Sections were stored at −80° C. prior to in situ hybridization.

Riboprobe Synthesis

The plasmid pCDNA3-TRHR2 was linearized using either XbaI or HindIII restriction enzymes, which cut in the polylinker on either side of the inserted cDNA. Sense and antisense TRHR-2 riboprobes were transcribed in vitro using either T7 or SP6 RNA polymerases (Pharmacia, Baie d'Urfe, Quebec), respectively in the presence of [$^{35}$S]UTP (~800 Ci/mmol; Amersham, Oakville, Ontario). Following transcription, the DNA template was digested with DNAse I (Pharmacia). Riboprobes were subsequently purified by phenol/chloroform/isoamyl alcohol extraction and precipitated in 70% ethanol containing ammonium acetate and tRNA. The quality of labeled riboprobes was verified by polyacrylamide-urea gel electrophoresis.

In Situ Hybridization

Sections were postfixed in 4% paraformaldehyde (BDH, Poole, England) in 0.1 M phosphate buffer (pH 7.4) for 10 min at room temperature (RT) and rinsed in 3 changes of 2×standard sodium citrate buffer (SSC: 0.15 M NaCl. 0.015 M sodium citrate, pH 7.0).

Sections were then equilibrated in 0.1 M triethanolamine, treated with 0.25% acetic anhydride in triethanolamine, rinsed in 2×SSC and dehydrated in an ethanol series (50–100%). Hybridization was performed in a buffer containing 75% formamide (Sigma, St. Louis, Mo.), 600 mM NaCl, 10 mM Tris (pH 7.5), 1 mM EDTA, 1×Denhardt's solution (Sigma), 50 µg/ml denatured salmon sperm DNA (Sigma), 50 µg/ml yeast tRNA (Sigma), 10% dextran sulfate (Sigma), 10 mM dithiothreitol and [$^{35}$S]UTP-labeled cRNA probes (10×10$^6$ cpm/ml) at 55° C. for 18 h in humidified chambers. Following hybridization, slides were rinsed in 2×SSC at RT, treated with 20 µg/ml RNase IA (Pharmacia) in RNase buffer (10 mM Tris, 500 mM NaCl, 1 mM EDTA, pH 7.5) for 45 min at RT and washed to a final stringency of 0.1×SSC at 65° C. Sections were then dehydrated and exposed to Biomax MR Kodak film for 10 days. Neuroanatomical structures were identified according to the Paxinos and Watson rat brain atlas (Paxinos et al., *The Rat Brain in Stereotaxic Coordinates*, Academic Press (1986)).

B. Results

The most prominent labeling for TRHR-2 was detected throughout the thalamus, with the anterior, centromedian, centrolateral, paracentral and ventroposteromedian (VPM) nuclei exhibiting the highest intensity (see Table 2). In the more caudal thalamus, the medial geniculate nucleus was also moderately labeled. In addition, layers III–V of the cerebral cortex were moderately labeled. The pontine nuclei as well as the Purkinje cell layer of the cerebellum also displayed a high density of TRHR-2 mRNA hybridization. More moderate labeling was detected in the medial amygdalar nucleus as well as in a specific portion of the lateral hypothalamic area which does correspond to well known nuclear boundaries. Moderate to weak hybridization was detected throughout the reticular formation of the brain stem. Other cephalic areas such as the hippocampus, the remaining hypothalamus, the pituitary gland and basal ganglia were generally devoid of labeling. In the spinal cord, TRHR-2 mRNA expression was restricted to the entire dorsal horn. This is in stark contrast to that of the known TRH receptor mRNA under the same conditions which appears to be present only in the hypothalamus, the anterior pituitary gland and some sparse neurons in the ventral horn of the spinal cord.

TABLE 2

Localization of TRHR-1 and TRHR-2 by In Situ Hybridization

| Tissue | TRHR-1 | TRHR-2 |
| --- | --- | --- |
| Pituitary Gland | | |
| anterior | +++ | − |
| intermediate | − | − |
| posterior | − | − |
| Spinal cord | | |
| dorsal horn | − | ++ |
| ventral horn | + | − |
| Brain | | |
| piriform cortex | + | − |
| amygdala | + | + |
| hypothalamic nuclei | + | − |
| thalamus | − | +++ |
| medial habenular n. | − | ++ |
| frontal & parietal cx. | − | ++ |
| pontine nuclei | − | +++ |
| cerebellum | − | +++ |

What is claimed is:

1. A substantially pure protein comprising the amino acid sequence of SEQ ID NO:2, wherein said protein comprises a receptor for thyrotropin-releasing hormone (TRH).

2. A substantially pure protein of claim 1, wherein said amino acid sequence is 352 residues in length and preferentially binds TRH.

3. A substantially pure protein wherein said protein has an amino acid sequence that consists essentially of the amino acid sequence of SEQ ID No:2.

4. A substantially pure protein of claim 3, wherein said protein preferentially binds TRH and is 352 amino acids in length.

5. A substantially pure protein of claim 2, wherein said protein has a sequence consisting of the amino acid sequence of SEQ ID NO:2.

6. An isolated recombinant thyrotropin-releasing hormone receptor, wherein said receptor is produced by transfecting a host cell with an expression vector comprising a polynucleotide encoding the protein of any one of claims 1–5 and expressing and isolating the protein, and wherein the protein is the receptor.

7. The recombinant thyrotropin-releasing hormone receptor of claim 6, wherein said host cell is a eukaryotic cell.

8. The recombinant thyrotropin-releasing hormone receptor of claim 7, wherein said eukaryotic cell is a mammalian cell.

* * * * *